United States Patent
Van Der Poel et al.

(10) Patent No.: US 7,786,889 B2
(45) Date of Patent: Aug. 31, 2010

(54) ATMOSPHERE DEVICE WITH USER INTERFACE FOR LIGHT AND FRAGRANCE CONTROL

(75) Inventors: Lucas L. D. Van Der Poel, Eindhoven (NL); Cristina Sala Camps, Eindhoven (NL)

(73) Assignees: Koninklijke Philips Electronics N.V., Eindhoven (NL); Sara Lee Household and Body Care Espana S.L., Barcelona (ES)

( * ) Notice: Subject to any disclaimer, the term of this patent is extended or adjusted under 35 U.S.C. 154(b) by 386 days.

(21) Appl. No.: 11/915,618

(22) PCT Filed: May 24, 2006

(86) PCT No.: PCT/IB2006/051662

§ 371 (c)(1), (2), (4) Date: Nov. 27, 2007

(87) PCT Pub. No.: WO2006/129250

PCT Pub. Date: Dec. 7, 2006

(65) Prior Publication Data

US 2008/0198577 A1    Aug. 21, 2008

(30) Foreign Application Priority Data

Jun. 1, 2005    (EP)    ................... 05104717

(51) Int. Cl.
G08B 5/00    (2006.01)
(52) U.S. Cl. .................... 340/815.4; 340/326; 340/332; 340/572.1; 362/101; 700/17; 700/283

(58) Field of Classification Search .............. 340/572.1, 340/332, 539.1, 326, 815.4; 239/306; 235/492; 700/17; 362/253, 101
See application file for complete search history.

(56) References Cited

U.S. PATENT DOCUMENTS

| | | | |
|---|---|---|---|
| 6,779,905 B1 | 8/2004 | Mazursky et al. | |
| 7,444,187 B2* | 10/2008 | Diederiks et al. | ............. 700/17 |
| 7,610,118 B2* | 10/2009 | Schramm et al. | ............ 700/283 |
| 2002/0045954 A1 | 4/2002 | Nose et al. | |
| 2003/0106260 A1 | 6/2003 | Airaudi et al. | |
| 2005/0036300 A1* | 2/2005 | Dowling et al. | ............. 362/101 |

FOREIGN PATENT DOCUMENTS

| | | |
|---|---|---|
| EP | 1468702 A1 | 10/2004 |
| WO | 9706479 | 2/1997 |
| WO | 2005107337 | 11/2005 |

* cited by examiner

*Primary Examiner*—Brent Swarthout
(74) *Attorney, Agent, or Firm*—Mark L. Beloborodov

(57) ABSTRACT

The present invention relates to an atmosphere device (1) with a user interface (3) for controlling the setting of a lighting unit (2a) and/or a fragrance unit (2b) of the atmosphere device (1), thus determining the atmosphere conditions in a room. The user interlace (3) is based on a system comprising a detecting device (4) and transponders (6). By bringing the transponders (6) within the range of detection by the detecting device (4), the transponders (6) will send a return signal, which signal controls the settings of the atmosphere device (1). Each transponder (6) is programmed to control a particular color or a specific light intensity and/or a particular odor spectrum and intensity.

19 Claims, 3 Drawing Sheets

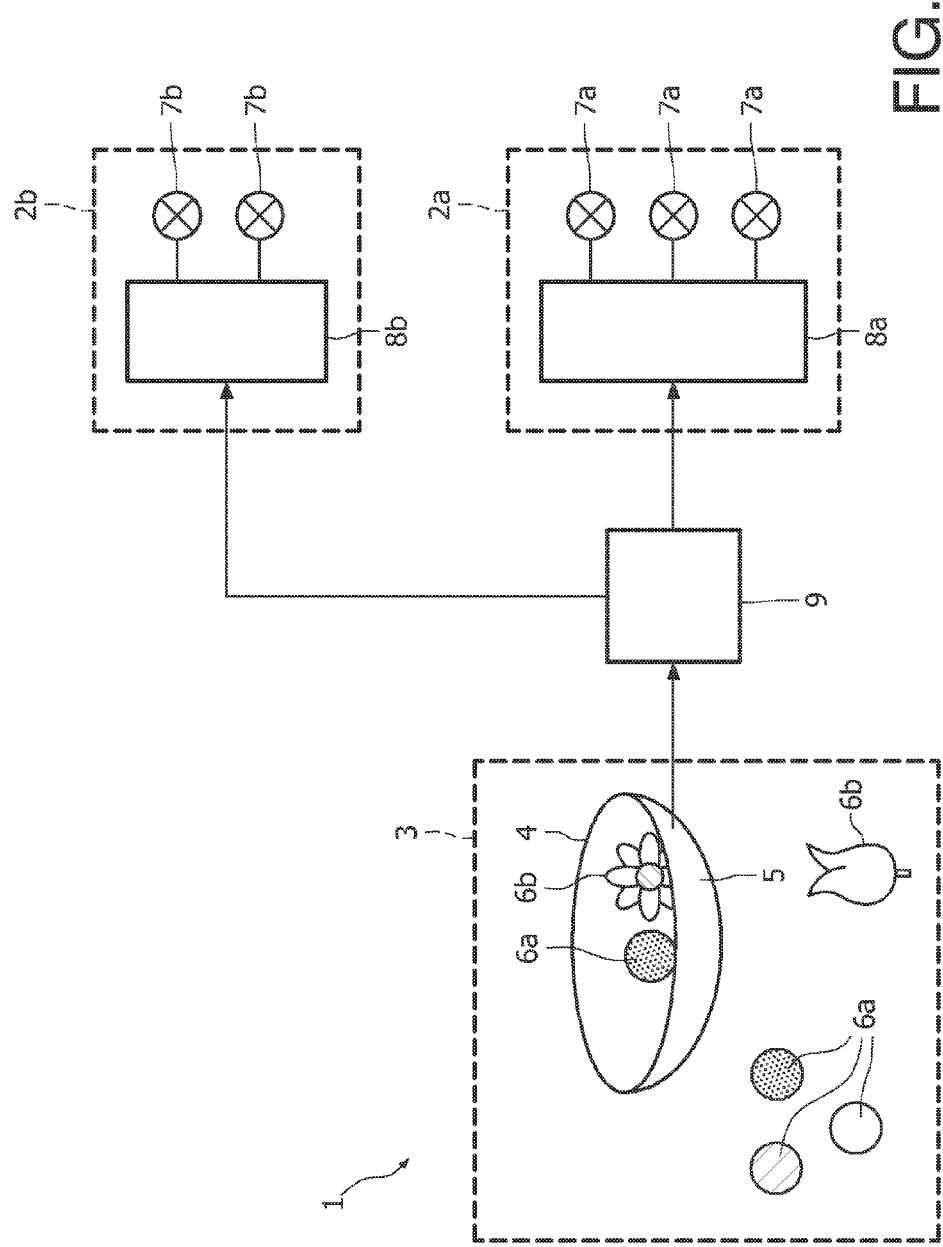

ATMOSPHERE DEVICE WITH USER INTERFACE FOR LIGHT AND FRAGRANCE CONTROL

The invention relates to an atmosphere device comprising a lighting unit, a fragrance unit and an interface for controlling both a setting of the lighting color and/or intensity of the lighting unit and a setting of the odor spectrum and/or intensity.

The invention further relates to a user interface for controlling an atmosphere device comprising an assembly of a lighting unit, a fragrance unit and a processing unit controlled by such a user interface and to a method of controlling an atmosphere device.

Current light sources mainly contain only one lighting color and can be controlled by switching them on or off or by dimming. In the near future, atmosphere devices comprising both light sources, which are capable of producing a whole spectrum of colored light, and fragrance sources, which are capable of producing a selected odor spectrum, will become commonplace, also in every household. These kinds of atmosphere devices will allow the creation of almost any color, odor and atmosphere, depending on the room or place to be cared for.

Consequently, control of such atmosphere devices will become more complex, because the user also has to control fragrance spectra and intensity besides the light intensity, brightness, and/or color aspects. As said control is new to many users, it is important that a control unit handling said control is easy to use.

It is a disadvantage of the prior-art technology that it does not provide an easy method of controlling atmosphere devices having a wide range of possible emission spectra.

It is an object of the present invention to provide an atmosphere device in which the above-mentioned disadvantages of the prior art are counteracted.

According to the present invention, this object is realized by an atmosphere device comprising a lighting unit, a fragrance unit and a user interface for controlling both a setting of the lighting color and/or intensity of the lighting unit and a setting of the odor spectrum and/or intensity of the fragrance unit, said user interface having a plurality of transponders and a detecting device for detecting transponders, each transponder being arranged to control a particular atmosphere setting and to assume a first position corresponding to a state in which said transponder is not detected by the detecting device, and a second position corresponding to a state in which said transponder is detected by the detecting device and sends a return signal, said return signal controlling both the lighting color and/or intensity of the lighting unit and the odor spectrum and/or intensity of the fragrance unit.

The invention is based on the recognition that by moving tangible objects—here referred to as transponders—with respect to a detecting device for transponders, it will become very easy for a user to change the ambient atmosphere, i.e. the odor spectrum and/or odor intensity, and/or the color and/or the intensity of a light source or a plurality of light sources, especially if each transponder corresponds to a particular odor and/or color. For instance, if a user wants to change the intensity of a certain color, the only thing he needs to do is to change a lighting transponder corresponding to this color from the first position to the second position, or vice versa. This movement of the lighting transponder will cause the lighting transponder to change its return signal, and this return signal is a measure of the change in lighting color. In a similar way, the odor spectrum can be easily controlled by a similar change of a transponder corresponding to a certain odor.

In a preferred embodiment, the particular lighting colors to be controlled comprise the primary colors red, green and blue. In the 1931-CIE chromaticity diagram, these primary colors form a triangle and all the colors within this triangle can be generated by adjusting the ratio of the intensities of these three primary light sources. In particular, this allows the choice of a wide range of color temperatures of white light, from cold light—like the light of halogen types of lamps—to warm light—like the light of conventional light bulbs. This is applicable to all kinds of light sources. Examples are incandescent lamps, HID-lamps, low mercury pressure discharge lamps, light-emitting diodes (LEDs); but the invention is not limited to these examples.

In another preferred embodiment, the odor spectra to be controlled comprise natural odors, for instance, the odors of flowers, plants, soaps, shampoos or perfumes, for instance, the odor of roses, lavender, orchids, freshly mown grass, sea water, coffee, freshly baked bread, Chanel No. 5™, Anaïs Anaïs™, etc. Alternatively, odors like the smell of burning rubber of accelerating cars, or the smell of smoking gun powder, are interesting when the atmosphere device is used in (automated) combination with television or computer images. It is particularly convenient when the fragrance transponders exhibit the look of the odor they represent, for instance, by having the shape of a flower, or forming a part of a perfume bottle, or showing a photograph of the sea.

A further embodiment is characterized in that the intensity of a lighting color and/or odor spectrum is proportional to the number of transponders arranged to control said color and assuming the second position. The arrangement of this embodiment is very intuitive for controlling an atmosphere device. It ensures that the more transponders are put in the second position, the more light and/or fragrance output is generated from this specific selection. The relation between the number of transponders may be chosen, for instance, linearly, i.e. the power is linearly proportional to the number of transponders. Another option is to establish an exponential relationship between the number of transponders in the second position and the power fed to the atmosphere device; this better resembles the perceptive aspects of the human senses.

In a further preferred embodiment, the transponders are RFID tags, each comprising an identification number, and the detecting device comprises an antenna arranged to send, in operation, an electromagnetic signal which will be received by the RFID tag, the return signal comprising the identification number of the RFID tag. For the transponders, it is preferred to choose Radio Frequency Identification tags (RFID tags). These tags are generally known and widely used, for instance, in security systems for shops in order to prevent theft. When brought from its first position—i.e. when it is not detected by the detecting device—to its second position—i.e. when it is detected by the detecting device, such a RFID tag will send its identification number or ID number as a return signal. This ID number can be coupled in a unique way to a change in color, odor spectrum or intensity, for instance, by means of a look-up table.

It will also be possible to couple ID numbers of transponders to change the light intensity proportionally with the already adjusted color, thus in a color-neutral way. Furthermore, it will be possible to use 'white' RFID-tags, which change the intensity by adding a certain amount of white light to the lighting unit; in most cases, this will change the color of the light. In order to make it comfortable to adjust such a lighting device, the transponders may be colored in the color they control. For example, such a system may comprise red, green and blue transponders for adjusting the primary colors, and white transponders for influencing the color setting by adding white light.

Furthermore, it is preferable that the control of the lighting color and intensity together with the odor spectrum and intensity is pre-arranged or programmed in such a way that illogic, incoherent and/or unpleasant combinations of lighting and fragrances are avoided. For instance, an illogic combination might be the fragrance of freshly baked bread with the lighting setting corresponding to a warm Mediterranean evening, or the combination of the smell of freshly baked bread with the smell of freshly mown grass. It is alternatively possible to pre-program very pleasant combinations of lighting and fragrance, for instance, the combination of a sunset/rise lighting-setting with an odor of coffee. Said pre-programmed combinations enhance the ease of use of the user interface and counteract unpleasant combinations.

An example of such an atmosphere device is characterized in that the detecting device is incorporated in a bowl-like container and the transponders are incorporated in tangible objects, a transponder being in its first position when it is outside the bowl-like container and in its second position when it is inside the bowl-like container. In this example, the transponders may be marbles which can be put on a bowl, and all the transponders in the bowl determine the color and intensity of the corresponding lighting unit and fragrance unit. Such a bowl may be placed on a table, just like a fruit bowl and can be a decorative object in a household interior.

Another example is characterized in that the transponders are provided with a switching element and are incorporated in tangible objects having at least a first side and a second side, the switch being off when the first side is up and the switch being on when the second side is up, a transponder being in its first position when the tangible object is positioned with its first side up and in its second position when the tangible object is positioned with its second side up. In this example, the transponders are transferred from their first position to their second position by just turning them upside down. This means that, in the case of the bowl-like container, all the transponders can always be inside this bowl, and the side which points up determines whether the transponders are active or not.

In the same way, the detecting device can be incorporated in, for instance, the edge or surface of a table, creating an atmosphere device for which all the transponders are just objects lying on the table within the area of the detecting device, and the lighting unit and fragrance unit are controlled by turning the transponders upside down.

The atmosphere device is further characterized in that it further comprises a processing unit for converting the return signals from the detecting device into an input value for both the lighting unit and the fragrance unit.

Each transponder which is put in its second position sends a return signal, which should be translated into the information needed for driving the lighting unit and/or the fragrance unit. This translation can be easily done by a processing unit, such as, fore instance, a personal computer. By way of example, the translation can be derived from a look-up table giving the relation between a series of return signals from a number of transponders to the corresponding lighting color and/or intensity of the lighting unit and the odor spectrum and odor intensity of the fragrance unit.

The invention further relates to a user interface for controlling a lighting unit and a fragrance unit of such an atmosphere device, an assembly of a lighting unit, a fragrance unit and a processing unit controlled by such a user interface, as well as to a method of controlling this lighting unit and fragrance unit.

These and other aspects of the invention are apparent from and will be elucidated by way of non-limitative examples with reference to the drawings and the embodiments described hereinafter.

In the drawings:

FIG. 1 is a schematic drawing of the atmosphere device according to the invention;

Figure 2A:
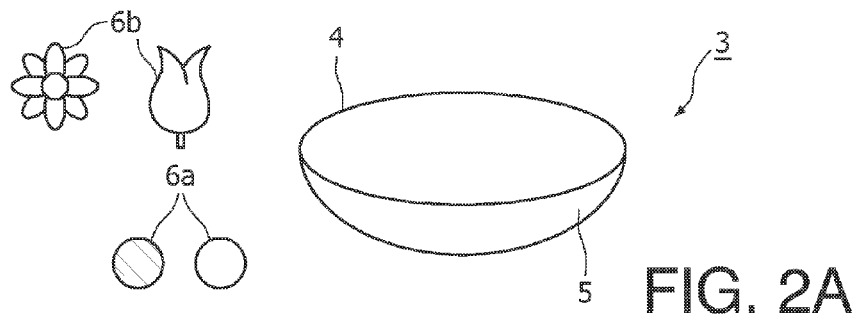
FIGS. 2A-2E show a first embodiment according to the invention.

FIG. 1 is a schematic overview of the different components of the atmosphere device 1 according to the present invention. The atmosphere device 1 comprises a lighting unit 2a, a fragrance unit 2b and a user interface 3. In the user interface 3, the following elements can be distinguished: a detecting device 4, such as, for instance, an antenna, and the transponders 6a, 6b. In this example, the detecting device 4 is mounted on a bowl 5. When, in this example, the transponders 6a, 6b are positioned outside the bowl, they are considered to be inactive, that is, they are not detected by the detecting device 4, while they are active when they are inside the bowl, that is, they are detected and the transponders send back a return signal. This return signal is converted into signals suitable for the driver circuits 8a, 8b to drive the light sources 7a and odor sources 7b, respectively. This conversion, i.e. from return signal to the choice of color and/or intensity of the lighting unit 2a and to the choice of odor and/or intensity from the fragrance unit 2b, is done by a processing unit 9—for instance, a personal computer—which may be a separate entity, but which may also be integrated in the user interface 3 or in the lighting unit 2a or in the fragrance unit 2b.

The user interface 3 can be seen as the remote control for the atmosphere setting in the room. The information derived from the return signal is sent to the processing unit 9 and the converted data is sent to the driver circuits 8a, 8b. This transfer of information can be realized by interconnecting the separate units, but it can also be done by transmitting the information in a wireless manner.

The light sources 7a may be LEDs of different colors, but also other light sources such as conventional lamps may be used. The odor sources 7b may be odor liquids/gases dispensed via odor dispensers such as spray nozzles, bottles, or other evaporators containing different odors, but also other odor sources such as impregnated solids may be used.

The present invention will now be described on the basis of two examples, but is not limited to these examples.

The user interface 3 of the first embodiment is shown in FIGS. 2A-2E. This user interface 3 has a bowl-like container 5 and a number of transponders 6a, 6b. The bowl-like container 5 may be a bowl, like a fruit bowl which can have a decorative value on a table, but also any other shape suitable for containing the transponders 6a, 6b. The bowl-like container 5 is provided with a detecting device 4; this may be a coil or an antenna which is mounted on the edge of the bowl-like container 5. This detecting device 4 has to be provided with a power supply and means for reading the information from the transponders 6a, 6b. For the transponders 6a, 6b, Radio Frequency IDentification (RFID) tags may be chosen. These RFID tags comprise an IC which can be programmed in such a way that it contains an ID number. The detecting device 4 comprises an antenna which sends an electromagnetic signal. This electromagnetic signal is received by the RFID tags which use the energy from this signal as power supply, whereupon the RFID tags send back a return signal with the identification as programmed in said RFID tag.

This information is sent to the processing unit in which it is converted into an input signal for appropriate parameters to drive the lighting unit and/or the fragrance unit. If the lighting unit is a LED system, these parameters may be the currents required to have a certain light output of the LEDs, or in the case of a large number of LEDs, these parameters may determine which LEDs are on and which are off. If the fragrance unit is a spray-nozzle system, these parameters may be the currents required to have a certain output of the odor of a respective spray nozzle, or in the case of a large number of spray nozzles, these parameters may determine which spray nozzles are on and which are off.

Figure 2B:
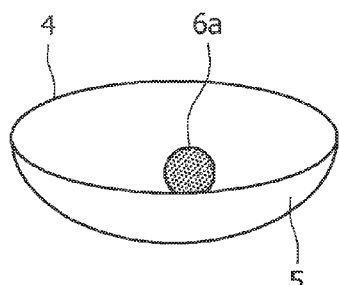
Figure 2C:
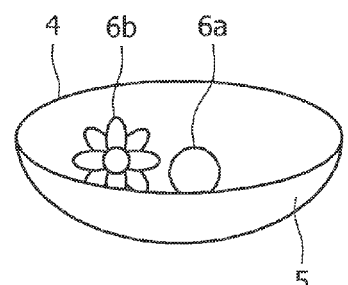

In FIG. 2A, the lighting unit and fragrance unit are in the off state, and all transponders 6a, 6b are outside the bowl-like container 5, which is referred to as their first or inactive position. In this example, the transponders 6a, 6b are contained in a shaped tangible object—hereinafter referred to as marbles—, the marbles 6a are colored in conformity with the contribution the marble makes to the desired color of the lighting and the marbles 6b have the shape of the flower and respective fragrance they represent, for instance, a daisy or a tulip. For instance, if the lighting unit comprises red, green and blue LEDs, the marbles are also red, green and blue colored. In FIGS. 2B and 2C, the lighting unit will emit light of only one color corresponding to the transponder 6a which is in its active position. In FIG. 2C, the fragrance unit of the atmosphere device will emit the fragrance of daisies.

Figure 2D:
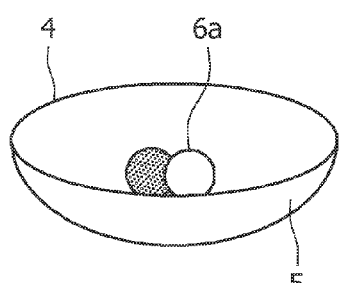
Figure 2E:
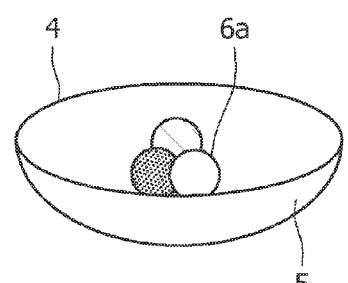

Addition of more transponders 6a to the bowl-like container 5 will give rise to mixing colors (and/or fragrances) as shown in FIGS. 2D and 2E. The intensity of the light/fragrance can be controlled by adding more marbles of the same color/shape. It may be chosen to increase the power on the LEDs linearly with the number of marbles of the corresponding colors which are active.

The sensitivity of the human eye shows a logarithmic behavior, i.e. the eye perceives the increase in intensity as linear when the power of the lighting sources is increased exponentially. For this reason, the processing unit may be programmed in such a way that the intensity increases exponentially by adding marbles to the bowl-like container 5.

When the bowl-like container 5 comprises a number of marbles chosen to give the desired color of lighting, and the intensity has to be increased, then marbles have to be added in the same ratio as are already present in the bowl-like container 5 in order to keep the same color of light. As a possible alternative for increasing the light intensity, use can be made of dedicated light-intensity marbles. For these marbles, the processing unit is programmed to increase the light intensity depending on the ratio of the already active marbles of different colors. This means that these dedicated light-intensity marbles do not change the lighting color.

The light/fragrance intensity can also be controlled by making marbles of different sizes: the larger the marble, the higher the light/fragrance intensity.

Furthermore, it will be possible to use marbles of mixed colors, for instance, a purple marble will drive a blue and red LED simultaneously, or alternatively to combine color and fragrance to yield a pleasant color plus fragrance combination. The processing unit may be pre-programmed to give a warning signal when an illogic/unpleasant combination of fragrances or color/fragrance is chosen. The warning signal may be, for instance, flickering of light and may have, for instance, the result that the odor dispensers of the fragrance unit will remain inactive.

Figure 3:
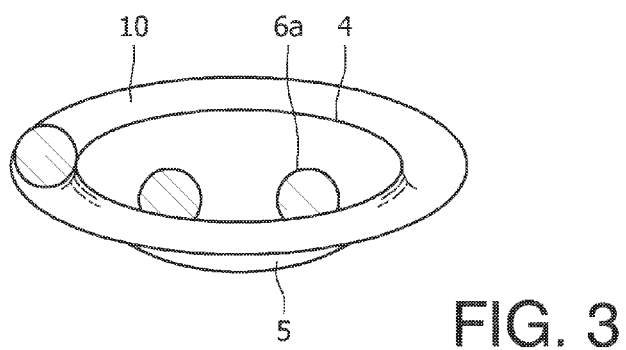
FIG. 3 is a variation of the first embodiment.

The marbles which are chosen to be inactive can be put in a separate box or just laid beside the bowl-like container. As an alternative, as shown in FIG. 3, a bowl-like container 5 can be used with a groove 10, which is positioned outside the region enclosed by the detecting device 4 and in which the inactive marbles can be put.

Figure 4:
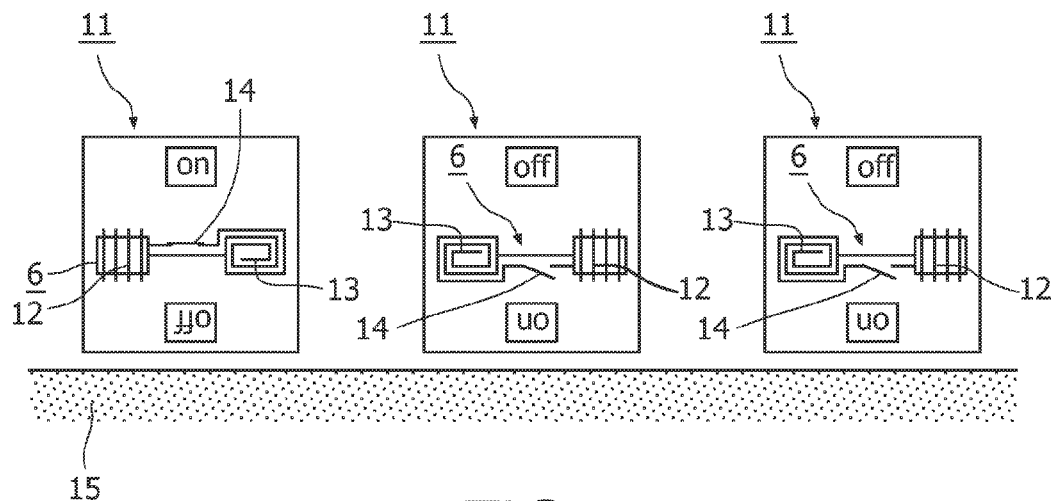
FIG. 4 shows a second embodiment according to the invention.

FIG. 4 shows a second embodiment of the present invention. In this example, the transponder 6, representing both the transponder for light 6a and for fragrance 6b, is incorporated in a cube 11 which is placed on a surface 15, for instance, a table. The detecting device 4 may be installed in the edge of the table top or in some region of the table top. Additionally, the transponders 6 are provided with a switching element 14 for enabling the transponder 6 to change from inactive to active. For instance, this switching element 14 may be a gravity switch, which is open—the off or inactive position—when the cube is in its first position, and closed—the on or active position—when the cube is turned upside down into its second position. In FIG. 4, the major parts of this type of transponder 6 can be distinguished inside the cube: the IC 12 with the programmed information, for instance, the ID number, the antenna 13 for receiving and returning signals, and the switching element 14.

In this embodiment, the cubes 11 can be colored in conformity with the color of the lighting to be controlled. In order to see what is the active and the inactive position of the cube, the side pointing up when the cube is inactive may be provided with just an indication of the appropriate color, e.g. black with a colored dot, while the side pointing up when the cube is active is fully colored. In FIG. 4, the left cube 11 is active, while the central and right cubes 11 are inactive. The way in which the lighting color and intensity is controlled is similar to the first embodiment, the difference is found in the way the transponders are transferred from their first position to their second position: in the first embodiment by putting the marbles in the bowl-like container 4, in the second embodiment by turning the cubes 11 upside down. The same or analogous way of controlling the fragrance is applicable for controlling the fragrance unit.

Figure 5:
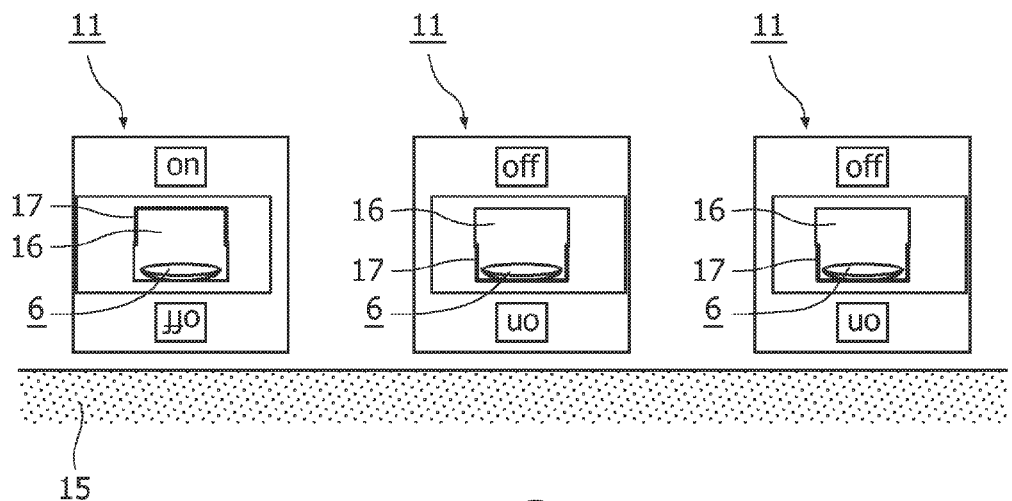
FIG. 5 is a variation of the second embodiment.

An alternative for the gravity switch is shown in FIG. 5. Here, the cube 11 is provided with a cavity 16. In this cavity 16, a transponder 6 is positioned which can move in this cavity 16. Furthermore, the cavity 16 is provided with a metal shielding 17 which covers half the cavity. In the left cube in FIG. 5, the shielding 17 covers the upper half of the cavity 16 when the cube 11 is in its second—active—position; in this orientation of the cube 11, the transponder 6 will be detected by the detecting device 4. When the cube 11 is turned upside down, as has been done for the central and right cubes of FIG. 5, the shielding 17 will cover the lower half of the cavity, the transponder 6 will fall down and the communication from the RFID tag will be disturbed so that the RFID tag will not be seen by the detecting device 4, i.e. it is inactive.

Here, too, the use of cubes does not limit this example; the tangible objects comprising the transponder 6 may also have different shapes such as, for instance, a flat disc, or a cylinder.

Furthermore, the two embodiments can be combined. For instance, if the transponder 6 is provided with a switching element 14, it can also be used in a bowl-like container 5. In that case, the transponders 6 remain in the bowl-like container 5 and are transferred from their first position to their second position by turning them upside down. Preferably, the transponders are then shaped as a disc or a pebble.

By dividing the surface 15 into a number of sub-areas, each sub-area being provided with a detecting device 4, the surface 15 can be used as a map of the room in which the lighting/fragrance has to be controlled. The relative position of the cubes 11 on the surface 15 determines which detecting device 4 sees the presence of said cubes 11 and can then be used to indicate in which specific part or parts of the room the lighting/fragrance is controlled.

The invention claimed is:

1. An atmosphere device comprising a lighting unit, a fragrance unit and an interface for controlling both a setting of at least one of the lighting color or intensity of the lighting unit and at least one of a setting of the odor spectrum or intensity of the fragrance unit, said user interface comprising a plurality of transponders and a detecting device for detecting transponders, each transponder being arranged to control a particular setting and to assume a first position corresponding to a state in which said transponder is not detected by the detecting device, and a second position corresponding to a state in which said transponder is detected by the detecting device and sends a return signal, said return signal controlling both at least one of the lighting color and/or intensity of the lighting unit and at least one of the odor spectrum or intensity of the fragrance unit, wherein the detecting device is incorporated in a bowl-like container and the transponders are incorporated in tangible objects, a transponder being in its first position when it is outside the bowl like container and in its second position when it is inside the bowl-like container, wherein each tangible lighting object has a color corresponding to the lighting color for which it is arranged to control.

2. An atmosphere device according to claim 1, wherein the lighting colors to be controlled comprise the primary colors red, green and blue.

3. An atmosphere device according to claim 1, wherein the odors to be controlled comprise at least one odor selected from the group of odors consisting of: flowers, plants, perfumes, soaps, fresh bread, (sea) water, burning rubber and gun powder.

4. An atmosphere device according to claim 1, wherein the lighting unit comprises at least one LED.

5. An atmosphere device according to claim 1, wherein the intensity of an atmosphere setting is proportional to the number of transponders arranged to control said setting and assuming the second position.

6. An atmosphere device according to claim 1, wherein the transponders are RFID tags, each comprising an identification number.

7. An atmosphere device according to claim 6, wherein the detecting device comprises an antenna arranged to send, in operation, an electromagnetic signal which will be received by the RFID tag, the return signal comprising the identification number of the RFID tag.

8. An atmosphere device according to claim 1, wherein each tangible fragrance object visualizes the odor which it is arranged to control.

9. An atmosphere device according to claim 1, wherein the tangible objects have the shape of marbles.

10. An atmosphere device comprising a lighting unit, a fragrance unit and an interface for controlling both a setting of at least one of the lighting color or intensity of the lighting unit and at least one of a setting of the odor spectrum or intensity of the fragrance unit, said user interface comprising a plurality of transponders and a detecting device for detecting transponders, each transponder being arranged to control a particular setting and to assume a first position corresponding to a state in which said transponder is not detected by the detecting device, and a second position corresponding to a state in which said transponder is detected by the detecting device and sends a return signal, said return signal controlling both at least one of the lighting color or intensity of the lighting unit and at least one of the odor spectrum or intensity of the fragrance unit, wherein the transponders are provided with a switching element and are incorporated in tangible objects having at least a first side and a second side, the switch being off when the first side is up and the switch being on when the second side is up, a transponder being in its first position when the tangible object is positioned with its first side up and in its second position when the tangible object is positioned with its second side up.

11. An atmosphere device according to claim 10, wherein the second side of each tangible lighting object is colored in conformity with the lighting color it controls, and the first side of said tangible lighting object bears an indication of said color.

12. An atmosphere device according to claim 10, wherein the second side of each tangible fragrance object visualizes the odor it controls, and the first side of said tangible object bears an indication of said odor.

13. An atmosphere device according to claim 10, wherein the detecting device is incorporated in a bowl-like container, and the transponders having the shape of disc-like tangible objects are positioned in said bowl-like container.

14. An atmosphere device according to claim 10, wherein the detecting device encloses a surface and the transponders having the shape of cube-like tangible objects are positioned on said surface.

15. An atmosphere device according to claim 1, further comprising a processing unit for converting the return signals from the detecting device into an input value for at least one of the lighting unit or the fragrance unit (2b).

16. An atmosphere device according to claim 10, wherein the lighting colors to be controlled comprise the primary colors red, green and blue.

17. An atmosphere device according to claim 10, wherein the lighting unit comprises at least one LED.

18. An atmosphere device according to claim 10, wherein the intensity of an atmosphere setting is proportional to the number of transponders arranged to control said setting and assuming the second position.

19. An atmosphere device according to claim 10, wherein the transponders comprise RFID tags, each having an identification number, and wherein the detecting device comprises an antenna arranged to send, in operation, an electromagnetic signal to be received by the RFID tags, the return signal comprising the identification number of at least one RFID tag.

* * * * *